US00PP08889P

United States Patent [19]

Danziger

[11] Patent Number: Plant 8,889

[45] Date of Patent: Sep. 13, 1994

[54] PETUNIA PLANT NAMED CAS 57

[75] Inventor: Gabriel Danziger, Post Beit Dagan, Israel

[73] Assignee: FLORFIS AG, Binningen, Switzerland

[21] Appl. No.: 162,464

[22] Filed: Dec. 7, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

*Attorney, Agent, or Firm*—Foley & Lardner

[57] ABSTRACT

A new and distinct cultivar of petunia plant named Cas 57, characterized by the combined feature of pink-violet flowers with white bordered edges and white throat with dark violet veins, vigorous growth habit, long, overhanging plant habit, and light green foliage.

2 Drawing Sheets

The present invention comprises a new and distinct cultivar of petunia, hereinafter referred to by the cultivar name Cas 57.

Cas 57 was originated from a hybridization made by the inventor Gabriel Danziger in a controlled breeding program in Moshav Mishmar Hashiva, Israel in 1992. The female parent was a seedling designated X 44. The male parent of Cas 57 was a seedling designated Y 27. Both parents are proprietary cultivars used in the breeding program.

Cas 57 was discovered and selected as one flowering plant within the progeny of the stated cross by Gabriel Danziger in 1992 in a controlled environment in Moshav Mishmar Hashiva, Israel.

The first act of asexual reproduction of Cas 57 was accomplished when vegetative cuttings were taken from the initial selection in December 1992 in a controlled environment in Moshav Mishmar Hashiva, Israel, by, or under the supervision of, Gabriel Danziger.

Horticultural examination of selected units initiated in December 1992 and continuing thereafter has demonstrated that the combination of characteristics are herein disclosed for Cas 57 are firmly fixed and are retained through successive generations of asexual reproduction.

Cas 57 has not been observed under all possible environmental conditions. The phenotype may vary significantly with variations in environment such as temperature, light intensity and day length without, however, any variations in genotype.

The following observations, measurements, and comparisons described plants grown in Hillscheid, Germany, under greenhouse conditions which approximate those generally used in commercial practice.

The following traits have been repeatedly observed and are determined to be basic characteristics of Cas 57, which in combination distinguish this petunia as a new and distinct cultivar:

1. Pink-violet flowers with white bordered edges.
2. White throat with dark veins.
3. Vigorous growth habit, with branches fully extending in all directions from center of plant.
4. Long, overhanging plant habit.
5. Light green foliage.

The accompanying photographic drawings show typical flower and foliage characteristics of Cas 57, with colors being as true as possible with illustrations of this type. The photograph on Sheet 1 illustrates Cas 57 cultivated in a hanging basket. The photo on Sheet 2 comprises an enlarged showing of single flowers of the new cultivar.

In the following description, color references are made to The Royal Horticultural Society Colour Chart. The color values were determined indoors in August. Flowers were taken from plants cultivated in hanging baskets in an open greenhouse in Hillscheid, Germany. For the description, the upper parts of the plants were observed or measured.

Classification:

*Botanical.*—A hybrid of the genus Petunia.

*Commercial.*—Petunia cv Cas 57.

INFLORESCENCE

Plant:

*Growth habit.*—Vigorous, drooping.

*Plant length.*—100–120 cm, measured from the base of the stems in the middle of the hanging basket to the tips of the hanging branches (28 week old plants).

*Blooming period.*—Begins 11 weeks after propagation of unrooted cuttings, continually flowering thereafter.

Stem:

*Thickness.*—Young branches, 2 mm; older branches 4–5 mm.

*Color.*—Light to medium green, 137 D.

*Pubescence.*—Present.

*Branching.*—10 branches per week.

*Length of internode.*—20–30 mm.

Leaf:

*Arrangement on stem.*—Opposite, arranged decussately on stem.

*Shape.*—Ovate to narrow-ovate.

*Size (average).*—52 mm long, 29 mm wide, based on largest leaves from a young stem of a plant in flower.

*Thickness.*—Thin.

*Color.*—Light to medium green, 137 C.

*Pubescence.*—Weak.

Flower:

*Orientation at opening.*—The bud and peduncle form an acute angle with the stem; the open flower and peduncle are oriented approximately at right angles to the stem.

*Type.*—Single.

*Shape.*—Not completely round, slightly zygomorph; upper lobes of the corolla a little shorter than the lower ones.

*Diameter.*—55–60 mm (comparatively small).

*Color.*—Upper (inner) surface at opening: 78 A. Under (outer) surface at opening: between 84 A and 78 C. Upper (inner) surface at pollen maturity: 78 A/B. Under (outer) surface at pollen maturity: 82 C. Throat (inner surface): white. Markings: dark violet veining, mainly in the upper half of the throat.

*Peduncle length.*—10–15 mm.

*Peduncle color.*—Light green.

*Reproductive organs.*—Pistil: 1 green. Stamens: 5. Anther: White, with white-blue pollen. Filament: White.

Resistance: Very good resistance to rain and good heat tolerance.

I claim:

1. A new and distinct cultivar of petunia plant named Cas 57, as illustrated and described.

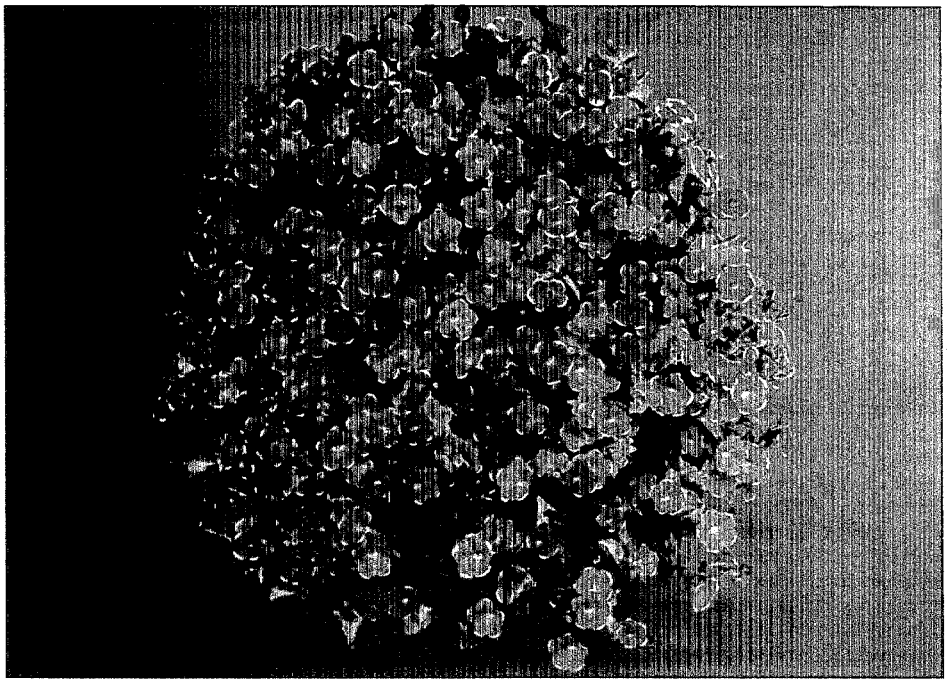

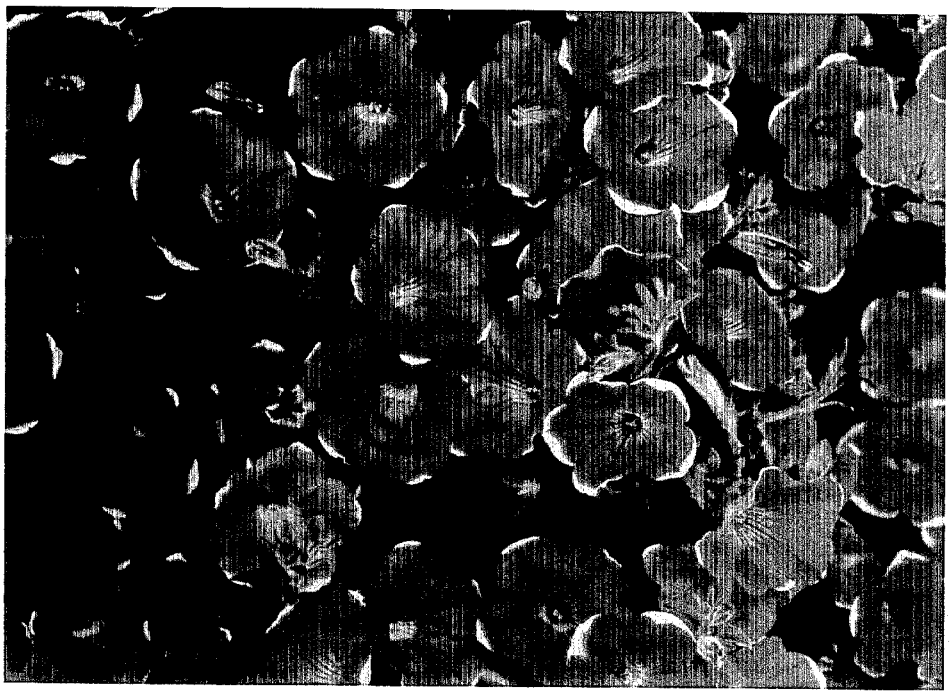

* * * * *